Figure 1:
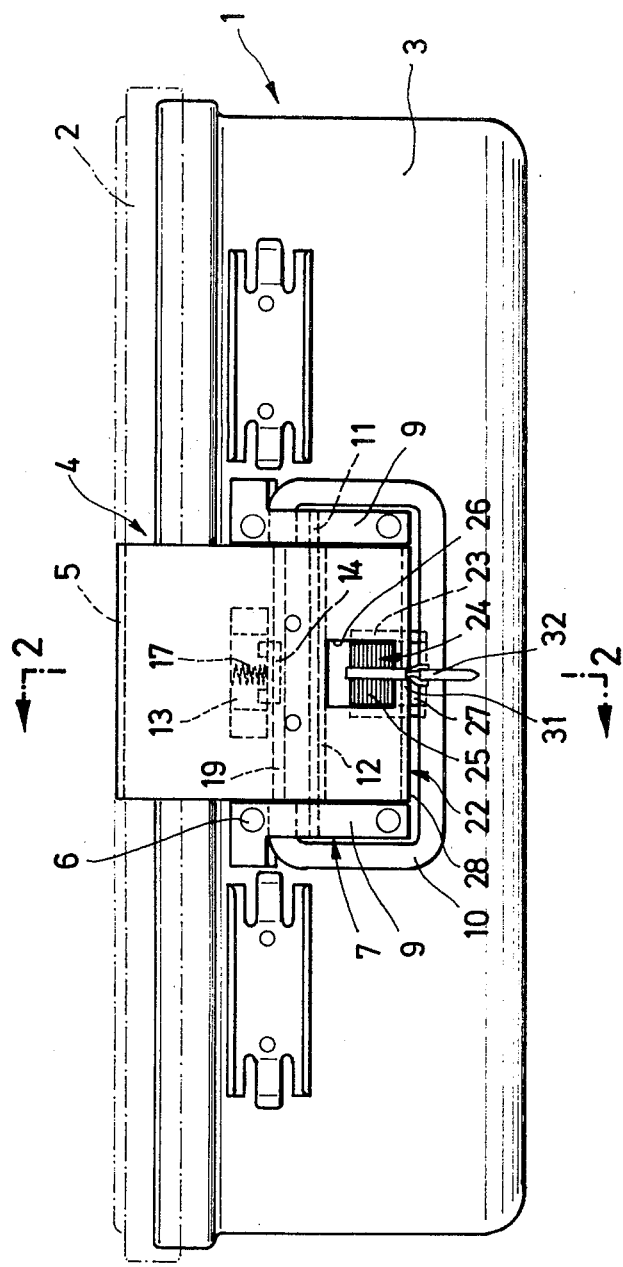

United States Patent [19]

Taschner

[11] 4,331,257
[45] May 25, 1982

[54] CLOSURE FOR A CONTAINER HAVING ADDITIONAL SECURING MEANS

[75] Inventor: Wolfgang Taschner, Tuttlingen, Fed. Rep. of Germany

[73] Assignee: Aesculap-Werke Aktiengesellschaft vormals Jetter & Scheerer, Fed. Rep. of Germany

[21] Appl. No.: 217,686

[22] Filed: Dec. 18, 1980

[51] Int. Cl.³ .............................................. B65D 45/16
[52] U.S. Cl. ..................................... 220/324; 220/214
[58] Field of Search ................. 220/214, 324; 292/113

[56] References Cited

U.S. PATENT DOCUMENTS

| | | | |
|---|---|---|---|
| 2,893,771 | 7/1959 | Claud-Mantle | 220/324 X |
| 3,088,623 | 5/1963 | Parker | 220/324 |
| 3,746,206 | 7/1973 | Utz | 220/214 |
| 3,934,518 | 1/1976 | Adler | 220/324 X |

*Primary Examiner*—George T. Hall
*Attorney, Agent, or Firm*—Kenway & Jenney

[57] ABSTRACT

A closure for a container used in hospitals to store and transport items. The closure includes a cable tie with a locking eyelet at one end. The other end of the cable tie passes through an opening in the closure and then locks into the eyelet. The locking eyelet has a retaining element that prevents the removal of the cable end. The cable, when thus secured, prevents an unintentional opening of the closure and therefore an unintentional movement of a lid of the container to an open position. Preferably the closure is a falling latch and the cable passes through an opening in the falling latch. It is also secured around or to other elements to prevent the falling latch from moving to a position where the lid can open.

8 Claims, 7 Drawing Figures

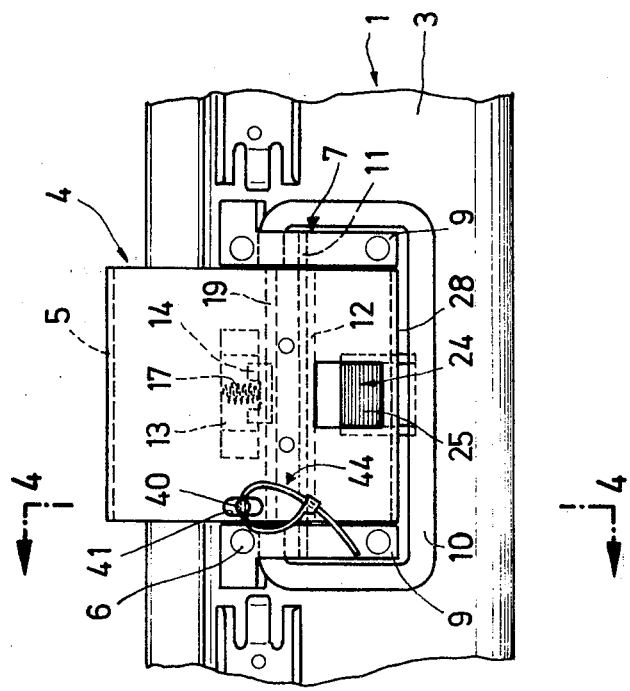
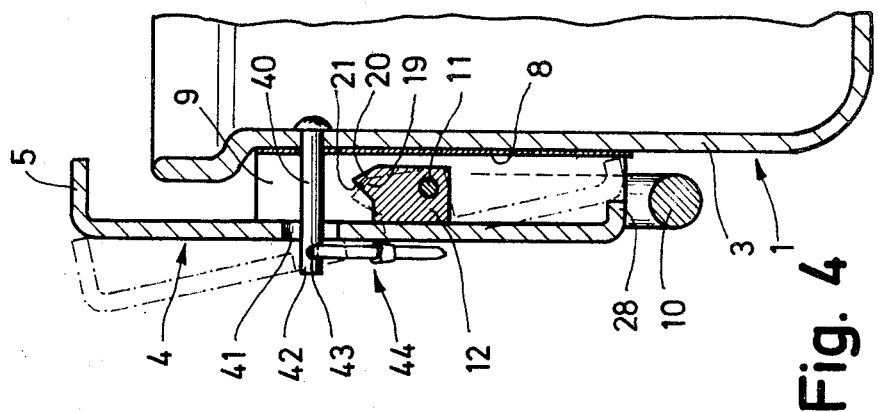

CLOSURE FOR A CONTAINER HAVING ADDITIONAL SECURING MEANS

This invention concerns a closure for a container for storing and transporting items needed in hospitals with a locking lid capable of pivoting around a horizontal axis supported on the side of the container and a movable falling latch supported between the side and the locking lid which can move into a locked position under the action of gravity, in which position the locking lid is secured against pivoting into the open position.

Such containers are used for the storage and transport of medical instruments, etc., which must be transported in these containers under sterile conditions. It is essential that these containers lock securely and reliably, and that the closures do not open unintentionally.

In known constructions of this type such as those known from German Pat. No. 2,207,339, a locking lid supported on the wall and capable of pivoting around a horizontal axis is located on the side wall of such a container, essentially parallel to the side wall, whose upper edge, bent inward, grasps a cover on the container or the bottom of a second container resting on the first container, and secures it on the container. The locking lid can pivot around the horizontal axis into an open position, in which the cover or the second container resting on the first container can be taken off. To secure the locking lid in the locked position in known devices of this kind, a snap mechanism with a snap lock is first provided, which is pushed against an elastic force when the locking lid is closed, and when the locking lid is fully closed, rests elastically against a sliding surface of the locking lid under the action of a spring, so that the locking lid is pivoted elastically into the locked position. However, this snap mechanism does not permit a reliable securing of the locking lid in the locked position, since the snap lock can be pushed against the spring force applied to it when the locking lid is opened, so that the locking lid can again be pivoted into the open position while overcoming this elastic force.

Furthermore, in known constructions of this kind, a falling latch is provided, which is mounted below the horizontal pivot axis between the locking lid and the wall and can move in a vertical direction, and which projects through an opening in the locking lid. This falling latch moves under the action of gravity into a lower position in which it is located between the bottom of the locking lid and the side wall in such a way that the swinging of the locking lid into the open position is impossible. By moving the falling latch against the force of gravity, it can be brought into a position in which the locking lid can be swung into the open position.

This falling latch does provide that the locking lid locks automatically when it is closed, but this locking can be easily reversed by pushing the falling latch manually. This can also occur unintentionally.

It is the purpose of this invention to find a possible method of locking permanently a closure of the known kind, so that the locking lid cannot swing into the open position unintentionally and unnoticed.

This problem is solved for a closure of the type described initially pursuant to the invention by providing means which reliably prevent the swinging of the locking lid from the locked position into the open position, wherein the means comprise cable ties with a locking eyelet with a retaining element at one end, and another end which can be introduced into it, which pass through at least one opening on a part of the closure and then are locked by inserting the one end of the cable tie into the locking eyelet so that the end is secured in the locking eyelet by the retaining element and can no longer be withdrawn from it, whereby the locked cable tie directly or indirectly prevents the motion of the locking lid into the open position.

By attaching the cable ties, the unintentional opening of the locking lid can be avoided with certainty. Since cable ties of this construction can no longer be opened when the one end has been inserted into the locking eyelet, it is necessary to destroy the cable tie to open it. For this reason, it is directly obvious that an undesired opening of the locking lid of a container has taken place; since this is possible only when the cable tie is destroyed, the absence of the cable tie reveals the undesired opening.

In a preferred embodiment of the closure pursuant to the invention, it is provided that the opening to receive the cable tie is located in the falling latch and the cable tie passes through this opening and around another part of the closure, in such a way that the falling latch is secured in its lower, locked position. At the same time, it is beneficial if the cable tie passes through the opening of the falling latch and around the lower edge of the locking lid. The falling latch is thus secured against motion relative to the locking lid and can no longer be moved into the upper position, the only position in which the locking lid can pivot.

The opening in the falling latch can run from top to bottom, and it is desirable if the opening in the falling latch is located so that the free end of the cable tie emerges behind the lower edge of the locking lid.

Preferably, the opening has a funnel-shaped flare at one end, so that the introduction of the free end of the cable tie is facilitated.

In another beneficial embodiment, it is provided that a projection is fastened on the side wall, which extends through an opening in the locking lid and has an opening in the section projecting out of the hole to receive the cable tie, which is located so that the opening is accessible for the insertion of the cable tie only when the locking lid is closed, and when the cable tie is inserted and locked, it rests against the locking lid when the locking lid moves in the direction of opening, and prevents a further motion of the locking lid into the open position.

Such a construction also makes it possible directly to prevent the opening of the locking lid, or to recognize that the locking lid has been opened unintentionally.

In another design of the closure pursuant to the invention, it can be provided that a locking element which can rotate outward from the front of the falling latch is connected to the falling latch, and can pivot upwardly in the lower, locked position of the falling latch, so that it strikes against a part of the closure when the falling latch moves against the force of gravity, and prevents the motion of the falling latch into the open position. It is advantageous in such a construction if the part of the locking element projecting above the falling latch and visible from the front of the falling latch through an opening in the locking lid only in this position of the locking element is colored for clear visibility. It can then be seen at a glance from the side of the container that the falling latch has moved into its lower position and cannot be moved upward without turning the locking element downward—if necessary, by using a tool.

Figure 2:
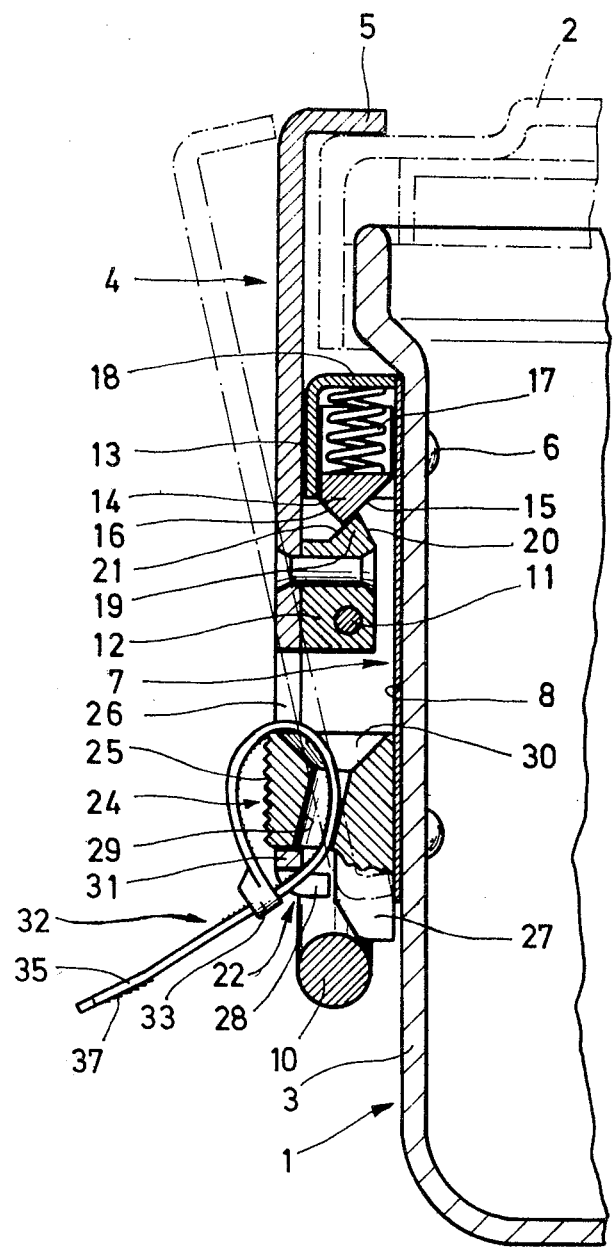
Figure 6:
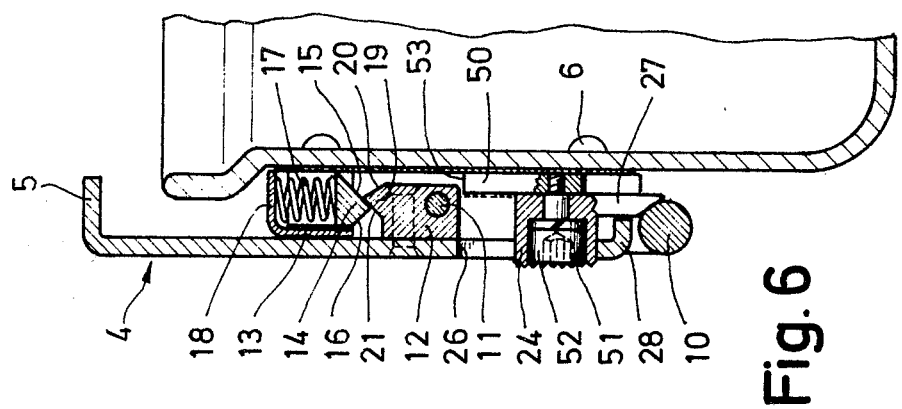
Figure 5:
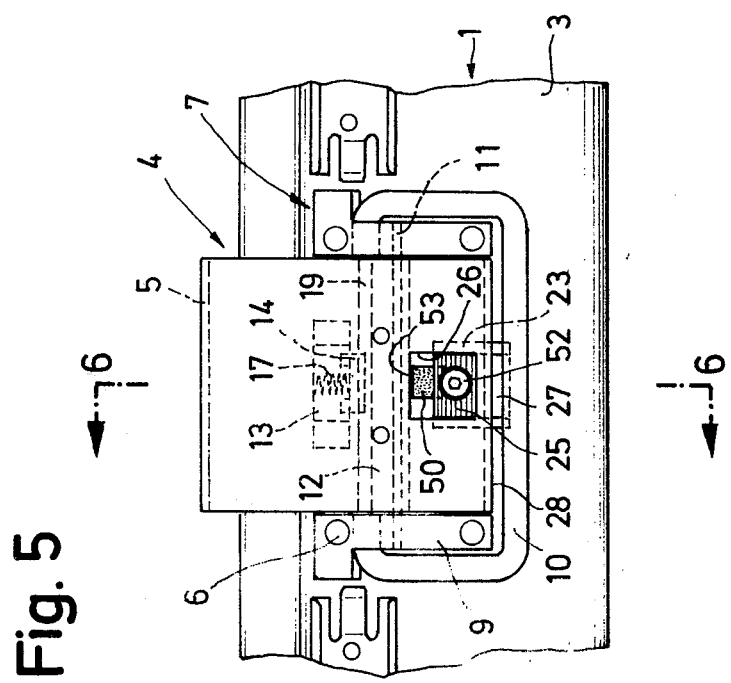

The following description of preferred forms of embodiment of the invention, in combination with the drawings, serves as a detailed explanation. The drawings show:

FIG. 1 a side view of a container with a closure pursuant to the invention;

FIG. 2 a sectional view along line 2—2 of FIG. 1;

FIG. 3 a partial view similar to FIG. 1 of another preferred example of embodiment of a closure pursuant to the invention;

FIG. 4 a sectional view along line 4—4 of FIG. 3;

FIG. 5 a partial view similar to FIG. 1 of another preferred example of embodiment of a closure pursuant to the invention;

FIG. 6 a sectional view along line 6—6 of FIG. 5; and

Figure 7:
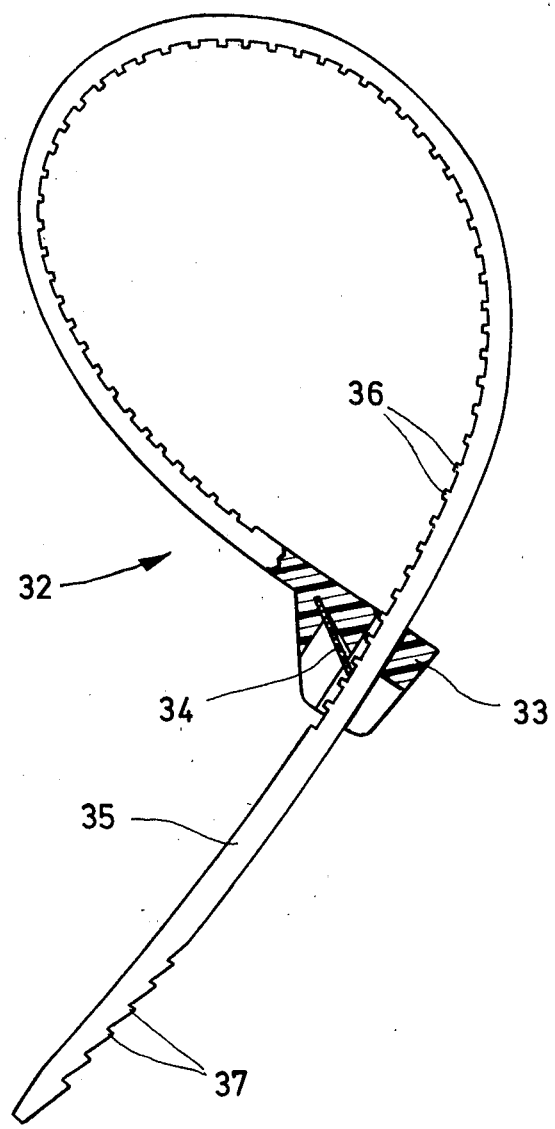

FIG. 7 a preferred design of a cable tie.

On a container 1 is set a cover 2, illustrated by dots and dashes in the drawings, which is secured in its closed position by a locking lid 4 oriented essentially parallel to a side wall 3, supported on the side wall, which can pivot around a horizontal axis. For this purpose an edge 5 of the locking lid 4 bent towards the side wall overlaps the cover. In the same way, instead of the cover, another container can be set down on the lower container; in this case, the edge 5 overlaps a projection on the bottom of the upper container.

For this purpose, a closure housing 7, which has a rear wall 8 against the side wall and two lateral wings 9, is fastened to the side wall 3 by rivets 6. The wings 9, on the one hand, serve as a holder for a pivoting handle 10, and on the other hand they carry a horizontal shaft 11 running parallel to the side wall which serves as a bearing for the locking lid 4. For this purpose, the side of the locking lid towards the side wall has a bearing housing 12 with a bore to receive the shaft 11. The pivot point of the locking lid is somewhat below the center of the locking lid.

A guide 13 for a spring lock 14 mounted for vertical motion is fastened to the rear wall 8 wherein the bottom of the spring lock is formed with a key shape and thus has two diagonally positioned sliding surfaces 15 and 16. The spring lock 14 is pushed downward with an elastic force by a compression spring 17 whose front end is supported at the base 18 of the guide 13. It acts jointly with a key-shaped knife-edge 19 of the bearing housing 12 which extends upward, which likewise has two sliding surfaces 20 and 21.

In the closed state of the locking lid, the inner sliding surface 15 of the spring lock lies against the outer sliding surface 21 of the bearing housing and thus presses the locking lid into the locked position under the action of the compression spring 17. In the open position, the outer sliding surface 16 of the spring lock rests against the inner sliding surface 20 of the bearing housing and thus presses the locking lid into the open position, with the lower end 22 of the locking lid resting against the rear wall 8 of the closure housing 7 (locking lid illustrated by dots and dashes in FIG. 2). In this way, therefore, the locking lid can be pivoted definitively from the open position into the locked position, with the spring lock pushed in its guide 13 against the force of the pressure spring 17 during the pivoting.

Beneath the bearing housing 12 on the rear wall 8 is a vertical sliding guide 23 for a falling latch 24 with a knurled gripping surface 25 extending through an opening 26 beneath the bearing housing in the locking lid. The falling latch 24 has an extension at its lower end which at the lower position of the falling latch is located between the rear wall 8 of the closure housing 7 on the one hand and between an edge 28 of the locking lid 4 bent inward on the other hand, in such a way that when the locking lid swings in the opening direction, the edge 28 strikes against the extension 27 and thus prevents a further swinging of the locking lid (FIG. 2). If the falling latch 24 is pushed against the force of gravity into its upper position, the extension 27 is removed between the rear wall 8 and the edge 28, so that the locking lid can thereafter be swung into the open position.

In the falling latch 24 is a bore 29 which passes through from top to bottom, which is slightly diagonal from top to bottom so that its distance from the side wall 3 is greater at the bottom end than at the top end. At the top end, the bore 29 is provided with an insertion funnel 30.

In the area beneath the falling latch 24 directly next to the exit of the bore 29, the edge 28 of the locking lid is removed, so that the locking lid in this area beneath the opening 26 has only a narrow strap 31.

As seen from the illustration of FIG. 2, the free end of a cable tie 32 can be introduced into the bore 29 in such a way that this free end emerges into the open at the bottom of the locking lid behind the strap 31 and can be drawn through the eyelet of the cable tie at this point. In this way, the cable tie passed through the bore 29 is guided around the strap 31 and when tightened, secures the falling lock 24 from moving out of the lower terminal position.

Cable ties suitable for this purpose are well known in themselves; in FIG. 7 is illustrated a preferred embodiment of such a cable tie. This consists preferably of a plastic strap 35 with the locking eyelet 33 molded onto one end. In the eyelet is located a tongue 34 oriented at an angle to the direction of insertion, which forms a retaining element, whose free end lies against the inserted strap. When the strap is inserted, it pushes aside the tongue which runs diagonally to the direction of advance, but if the strap is pulled in the opposite direction, the tongue cuts into the strap and prevents the strap from being pulled out. To reinforce this locking, the strap can have a number of cross ribs 36. Cross ribs 37 can also be located at the free end of the strap; these facilitate the gripping of the free end of the strap and prevent slipping when it is pulled tight.

It is understood that cable ties of different construction can also be used within the scope of the invention, but it is essential that these cable ties can be opened only by their destruction after introduction of the free end into the locking eyelet, and that therefore the free end can no longer be withdrawn from the eyelet.

In FIGS. 3 and 4 is illustrated a different example of embodiment of a container closure. This construction is largely similar to that of the closure of FIGS. 1 and 2; corresponding parts, for this reason, have the same reference symbols.

In contrast to the closure described with FIGS. 1 and 2, the falling latch has no bore to receive a cable tie. In this embodiment, the falling latch cannot be secured separately in its lower position.

In this embodiment, a pin 40 fastened to the side wall and extending outward from it, which projects through an opening 41 through the locking lid, is used to secure the locking lid. At its free end 42 projecting above the locking lid, this pin 40 has a transverse bore 43 through which a cable tie 44 can be introduced. If this cable tie 44 is locked in the manner apparent from the drawing, it rests against the outer wall of the locking lid when the locking lid is swung into the open position, and prevents a further swinging towards the open position. The arrangement of the bore 43 is such that the cable tie is located directly against the outside of the locking lid when it is locked.

Another preferred example of a closure is illustrated in FIGS. 5 and 6. This closure again is largely similar to that in FIGS. 1 and 2, and corresponding parts therefore have the same reference symbols.

In contrast to the embodiment of FIGS. 1 and 2, the falling latch has a locking element 50 on its side turned towards the side wall 3, which is mounted on the falling latch so that it can pivot around a horizontal axis standing perpendicular to the side wall 3. For this purpose, the falling latch has a stepped bore 51 in which is inserted a hexagon sockethead bolt. This bolt is connected to the locking element 50 so that it cannot turn.

When the falling latch is in its lower position, the locking element can be rotated with the help of the bolt 52 in such a way that one edge 53 of the locking element is located directly beneath the bearing housing 12. In this position, the motion of the falling latch out of the lower position is prevented, since in case of such a motion, the edge 53 strikes against the bearing housing. To make it possible for the falling latch to move, the locking element 50 must first be brought into a transverse position, in which it no longer projects above the upper edge of the falling latch, so that this can henceforth be pushed freely in the direction towards the bearing housing.

The surface of the locking element away from the side wall is colored for clear visibility in the area in which it projects above the falling latch in the locked position, so that a user can immediately discern through the opening 26 in the locking lid 4, whether the falling latch is blocked from moving towards the bearing housing or not. This construction in particular makes possible a reliable inspection of the locked condition of a container.

I claim:

1. Closure for a container to store and transport items needed in hospitals, with a locking lid, supported on the side of the container, which can pivot around a horizontal axis, and an adjustable falling latch supported between the side and the locking lid, which can move under the action of gravity into a locking position in which the locking lid is firmly fixed against swinging into the open position, characterized by the fact that means are provided to prevent reliably the swinging of the locking lid (4) from the closed position into the open position, and that the means comprise cable ties (32, 44) with a locking eyelet (33) with a retaining element (34) at one end and another end which can be introduced into it, which are passed through at least one opening (29; 43) on one part (24; 40) of the closure and are then locked by pushing one end of the cable tie (32; 44) into the locking eyelet (33), so that the end is fixed in the locking eyelet (33) by the retaining element (34) and can no longer be pulled out of it, whereby the motion of the locking lid (4) into the open position is directly or indirectly prevented by the locked cable tie (32, 44).

2. Closure pursuant to claim 1, characterized by the fact that the opening (29) to receive the cable tie (32) is located in the falling latch (24) and the cable tie (32) is fed through this opening (29) and around another part (31) of the closure in such a way that the falling latch (24) is secured in its lower, locked position.

3. Closure pursuant to claim 2, characterized by the fact that the cable tie (32) is fed through the opening (29) of the falling latch (24) and around the lower edge (31) of the locking lid (4).

4. Closure pursuant to claim 3, characterized by the fact that the opening (29) in the falling latch (24) extends from top to bottom.

5. Closure pursuant to claim 4, characterized by the fact that the opening (29) in the falling latch (24) is located so that the free end of the cable tie (32) emerges behind the bottom edge (31) of the locking lid (4).

6. Closure pursuant to claim 2, characterized by the fact that the opening (29) has a funnel-shaped flare (30) at one end, so that the introduction of the free end of the cable tie (32) is facilitated.

7. Closure pursuant to claim 1, characterized by the fact that a projection (40) is fastened to the wall and extends through a hole (41) in the locking lid and has an opening (43) to receive the cable tie (44) in the section extending out of the hole (41), which is located so that the opening (43) for pushing in the cable tie (44) is accessible only when the locking lid (4) is closed, and when the cable tie (44) is pushed in and locked, it rests on the locking lid (4) when the locking lid (4) moves in the direction of opening and prevents a further motion of the locking lid (4) into the open position.

8. Closure pursuant to claim 1, characterized by the fact that a rotatable locking element (50) is connected to the falling latch (24) and can turn upward in the lower, locked position of the falling latch (24) so that it strikes against a part (12) of the closure when the falling latch (24) moves against the force of gravity and prevents the motion of the falling latch (24) into the open position, and that the part of the locking element (50) projecting above the falling latch (24) and visible from the front of the falling latch (24) through an opening (26) of the locking lid (4) only in this position of the locking element (50), is colored for distinct visibility.

* * * * *